United States Patent
Ota et al.

(10) Patent No.: US 12,306,352 B2
(45) Date of Patent: May 20, 2025

(54) ULTRASOUND DIAGNOSTIC APPARATUS, METHOD OF CONTROLLING ULTRASOUND DIAGNOSTIC APPARATUS, AND NON-TRANSITORY COMPUTER-READABLE RECORDING MEDIUM STORING THEREIN COMPUTER-READABLE PROGRAM FOR CONTROLLING ULTRASOUND DIAGNOSTIC APPARATUS

(71) Applicant: KONICA MINOLTA, INC., Tokyo (JP)

(72) Inventors: Kazushi Ota, Tokyo (JP); Tomohito Sakai, Kanagawa (JP); Mutsuhiro Akahane, Tokyo (JP)

(73) Assignee: KONICA MINOLTA, INC., Tokyo (JP)

(*) Notice: Subject to any disclaimer, the term of this patent is extended or adjusted under 35 U.S.C. 154(b) by 326 days.

(21) Appl. No.: 17/730,998

(22) Filed: Apr. 27, 2022

(65) Prior Publication Data

US 2022/0370044 A1   Nov. 24, 2022

(30) Foreign Application Priority Data

May 19, 2021   (JP) .................. 2021-084680

(51) Int. Cl.
*A61B 8/00*   (2006.01)
*A61B 8/08*   (2006.01)
(Continued)

(52) U.S. Cl.
CPC ............ *G01S 7/5205* (2013.01); *A61B 8/465* (2013.01); *A61B 8/58* (2013.01); *G01S 15/8915* (2013.01); *G01S 7/52074* (2013.01)

(58) Field of Classification Search
USPC ......................................................... 73/596
See application file for complete search history.

(56) References Cited

U.S. PATENT DOCUMENTS 5,318,449 A * 6/1994 Schoell .................. F02B 77/08
                                                  123/480
5,517,994 A * 5/1996 Burke ................... G01S 7/5205
                                                  600/443
(Continued)

FOREIGN PATENT DOCUMENTS

JP   2009178262 A   8/2009
JP   2009285175 A   12/2009
(Continued)

OTHER PUBLICATIONS

Japanese Office Action (and an English language translation thereof) dated Dec. 10, 2024, issued in counterpart Japanese Application No. 2021-084680.

*Primary Examiner* — Clayton E. LaBalle
*Assistant Examiner* — Warren K Fenwick
(74) *Attorney, Agent, or Firm* — Holtz, Holtz & Volek PC (57) ABSTRACT

Provided is an ultrasound diagnostic apparatus for obtaining a tomographic image of a subject by transmitting and receiving an ultrasound with an ultrasound probe, the ultrasound diagnostic apparatus including: a hardware processor that: causes transmission and reception of an ultrasound for a probe element check with respect to each of a plurality of piezoelectric elements included in the ultrasound probe; converts signal features of reception signals obtained respectively in the plurality of piezoelectric elements at the time of the probe element check into image information indicating deterioration degrees of the plurality of piezoelectric elements, separately; and displays, based on a result of the conversion, a probe-condition mapping image expressed in a bar form by mapping images indicating the deterioration (Continued)

degrees of the plurality of piezoelectric elements in a row according to an arrangement of the plurality of piezoelectric elements in the ultrasound probe.

12 Claims, 10 Drawing Sheets (51) Int. Cl.
*A61B 8/13* (2006.01)
*G01S 7/52* (2006.01)
*G01S 15/89* (2006.01)

(56) References Cited

U.S. PATENT DOCUMENTS

| | | | |
|---|---|---|---|
| 10,028,729 B2* | 7/2018 | Beaty | G01S 7/5205 |
| 11,452,507 B2* | 9/2022 | Bulte | A61B 8/587 |
| 11,918,419 B2 | 3/2024 | Tezuka et al. | |
| 2009/0299183 A1 | 12/2009 | Kozai | |
| 2016/0131746 A1 | 5/2016 | Beaty et al. | |
| 2024/0180526 A1 | 6/2024 | Tezuka et al. | |

FOREIGN PATENT DOCUMENTS

| | | |
|---|---|---|
| JP | 2012139460 A | 7/2012 |
| JP | 2019097882 A | 6/2019 |
| JP | 2021178112 A | 11/2021 |

* cited by examiner

| Element No. | Reception level |
|---|---|
| 1 | 0.405 |
| 2 | 0.387 |
| 3 | 0.407 |
| 4 | 0.410 |
| 5 | 0.401 |
| 6 | 0.369 |
| 7 | 0.403 |
| 8 | 0.387 |
| 9 | 0.395 |
| 10 | 0.410 |
| 11 | 0.391 |
| 12 | 0.397 |
| 13 | 0.384 |
| 14 | 0.402 |
| 15 | 0.424 |
| 16 | 0.384 |
| 17 | 0.399 |
| 18 | 0.389 |
| 19 | 0.410 |
| 20 | 0.414 |

ULTRASOUND DIAGNOSTIC APPARATUS, METHOD OF CONTROLLING ULTRASOUND DIAGNOSTIC APPARATUS, AND NON-TRANSITORY COMPUTER-READABLE RECORDING MEDIUM STORING THEREIN COMPUTER-READABLE PROGRAM FOR CONTROLLING ULTRASOUND DIAGNOSTIC APPARATUS

CROSS REFERENCE TO RELATED APPLICATIONS

The entire disclosure of Japanese Patent Application No. 2021-084680 filed on May 19, 2021 is incorporated herein by reference in its entirety.

BACKGROUND

Technological Field

The present disclosure relates to an ultrasound diagnostic apparatus, a method of controlling an ultrasound diagnostic apparatus, and a non-transitory computer-readable recording medium storing therein a computer-readable program for controlling an ultrasound diagnostic apparatus.

Description of Related Art

An ultrasound diagnostic apparatus is widely used as a non-invasive method for obtaining image information in a body. The ultrasound diagnostic apparatus of this type detects reflection characteristics of ultrasound at various positions inside a subject by transmitting and receiving the ultrasound with an ultrasound probe, and thereby generates a tomographic image of the subject. Incidentally, the ultrasound probe is generally configured by an arrayed transducer including a plurality of piezoelectric elements, and each of the plurality of piezoelectric elements is provided with a function for transmitting and receiving the ultrasound separately.

Any piezoelectric element of an ultrasound probe may be damaged by impact such as dropping. Even in normal use, the piezoelectric elements will be less sensitive due to deterioration over time. Hence, the ultrasound diagnostic apparatus of this type is generally provided with a function of executing a probe element check of the ultrasound probe, and it is thus possible to check whether probe performance is appropriately guaranteed in practical use (see, for example, Patent Literature (hereinafter referred to as "PTL") 1 (US Patent Application Publication No. 2016/0131746).

Figure 1:
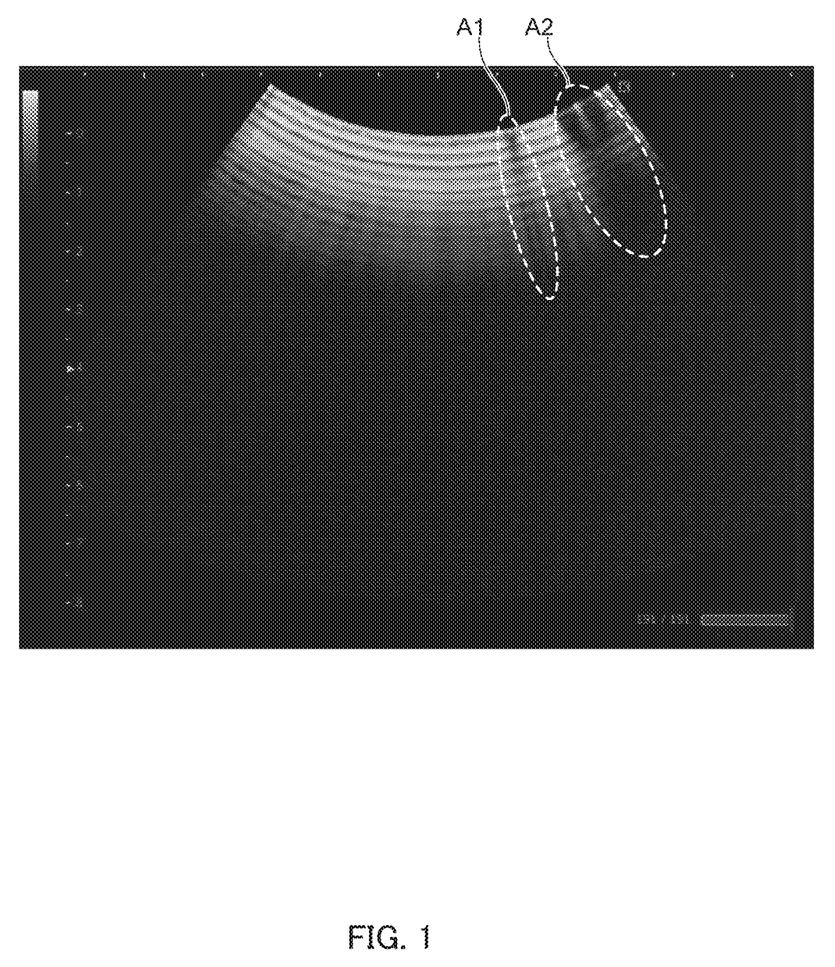
FIG. 1 illustrates an exemplary diagnostic image captured by an ultrasound probe with deteriorated piezoelectric elements (here, diagnostic image captured by probe element check using airborne radiation)

FIG. 1 illustrates an exemplary airborne radiation image captured by an ultrasound probe with deteriorated piezoelectric elements. In the diagnostic image of FIG. 1, areas of A1 and A2 are unclear images as a result of capturing by the piezoelectric elements in a deteriorated condition. In particular, image quality of the area of A2 is largely deteriorated because a plurality of neighboring piezoelectric elements is deteriorated.

Meanwhile, an effect of deterioration of the piezoelectric elements on a diagnostic image also depends on a deterioration degree thereof, and, in general, users determine when to repair or replace ultrasound probes based on a check result of the probe element check and intuition when viewing the diagnostic images.

Incidentally, in order to enable execution of the probe element check (hereinafter, also referred to as "element check") on a daily basis, in this type of ultrasound diagnostic apparatus, there has been demand for making the check result intuitively understandable not only by skilled engineers but also by common users.

However, in the ultrasound diagnostic apparatus according to the related art such as PTL 1, the check result of the probe element check is displayed in such a manner that a sensitivity level of each piezoelectric element of the ultrasound probe is displayed as a list or as a signal waveform; thus, it is impossible for anyone other than skilled engineers to determine what kind of abnormality has occurred in the ultrasound probe and whether the abnormality is a failure that requires repair or deterioration that is small enough to be acceptable.

On the other hand, considering the actual use forms of ultrasound diagnostic apparatuses, providing information on whether repair of an ultrasound probe is necessary, as a check result of the probe element check, alone lacks in practicality. In other words, the check result needs to be one by which a user can recognize the deterioration degree of the piezoelectric elements of the ultrasound probe.

SUMMARY

The present disclosure has been made in view of the above-described problems, and an object thereof is to provide an ultrasound diagnostic apparatus, a method of controlling an ultrasound diagnostic apparatus, and a non-transitory computer-readable recording medium storing therein a computer-readable program for controlling an ultrasound diagnostic apparatus, which are capable of providing information on a check result of a probe element check in a manner that is more intuitively understandable by a user.

To achieve at least one of the abovementioned objects, according to an aspect of the present invention, an ultrasound diagnostic apparatus reflecting one aspect of the present invention is an apparatus for generating a tomographic image of a subject by transmitting and receiving an ultrasound, the ultrasound diagnostic apparatus including: a hardware processor that:
  causes each of a plurality of piezoelectric elements included in the ultrasound probe to execute transmission and reception of an ultrasound for a probe element check;
  converts signal features of reception signals obtained respectively in the plurality of piezoelectric elements at the time of the probe element check into information about images indicating deterioration degrees of the plurality of piezoelectric elements, separately; and
  displays, based on a result of the conversion, a probe-condition mapping image expressed in a bar form by mapping the images indicating the deterioration degrees of the plurality of piezoelectric elements in a row according to an arrangement of the plurality of piezoelectric elements in the ultrasound probe.

To achieve at least one of the abovementioned objects, according to an aspect of the present invention, a method reflecting one aspect of the present invention is a method of controlling an ultrasound diagnostic apparatus for obtaining a tomographic image of a subject by transmitting and receiving an ultrasound with an ultrasound probe, the method including:
  causing each of a plurality of piezoelectric elements included in the ultrasound probe to execute transmission and reception of an ultrasound for a probe element check;

converting signal features of reception signals obtained respectively in the plurality of piezoelectric elements at the time of the probe element check into information about images indicating deterioration degrees of the plurality of piezoelectric elements, separately; and displaying, based on a result of the conversion, a probe-condition mapping image expressed in a bar form by mapping the images indicating the deterioration degrees of the plurality of piezoelectric elements in a row according to an arrangement of the plurality of piezoelectric elements in the ultrasound probe.

To achieve at least one of the abovementioned objects, according to an aspect of the present invention, a non-transitory computer-readable recording medium reflecting one aspect of the present invention is a medium storing therein a computer-readable program for controlling an ultrasound diagnostic apparatus for generating a tomographic image of a subject by transmitting and receiving an ultrasound, the program causing a computer to perform processing including:

causing each of a plurality of piezoelectric elements included in the ultrasound probe to execute transmission and reception of an ultrasound for a probe element check;

converting signal features of reception signals obtained respectively in the plurality of piezoelectric elements at the time of the probe element check into information about images indicating deterioration degrees of the plurality of piezoelectric elements, separately; and displaying, based on a result of the conversion, a probe-condition mapping image expressed in a bar form by mapping the images indicating the deterioration degrees of the plurality of piezoelectric elements in a row according to an arrangement of the plurality of piezoelectric elements in the ultrasound probe.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

Hereinafter, a preferred embodiment of the present disclosure will be described in detail with reference to the attached drawings. Note that elements having substantially the same functions are assigned the same reference numerals in the description and drawings to omit duplicated descriptions thereof.

[Overall Configuration of Ultrasound Diagnostic Apparatus]

In the following, with reference to FIGS. 2 and 3, a description will be given of an overall configuration of an ultrasound diagnostic apparatus (hereinafter referred to as "ultrasound diagnostic apparatus 1") according to the embodiment of the present invention.

Figure 2:
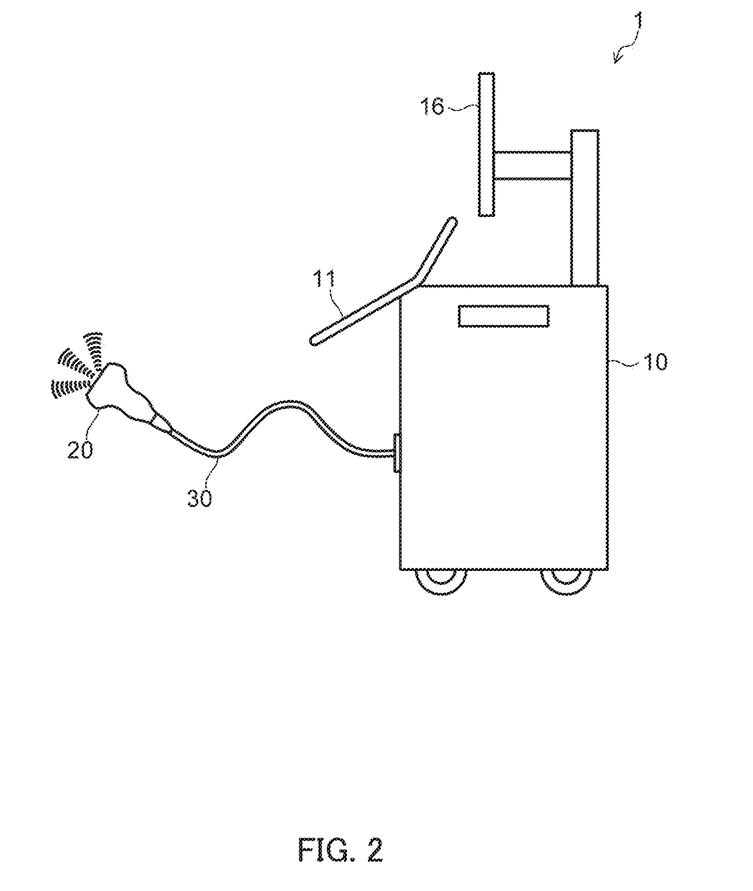
FIG. 2 illustrates an exemplary external view of an ultrasound diagnostic apparatus according to an embodiment of the present invention.
Figure 3:
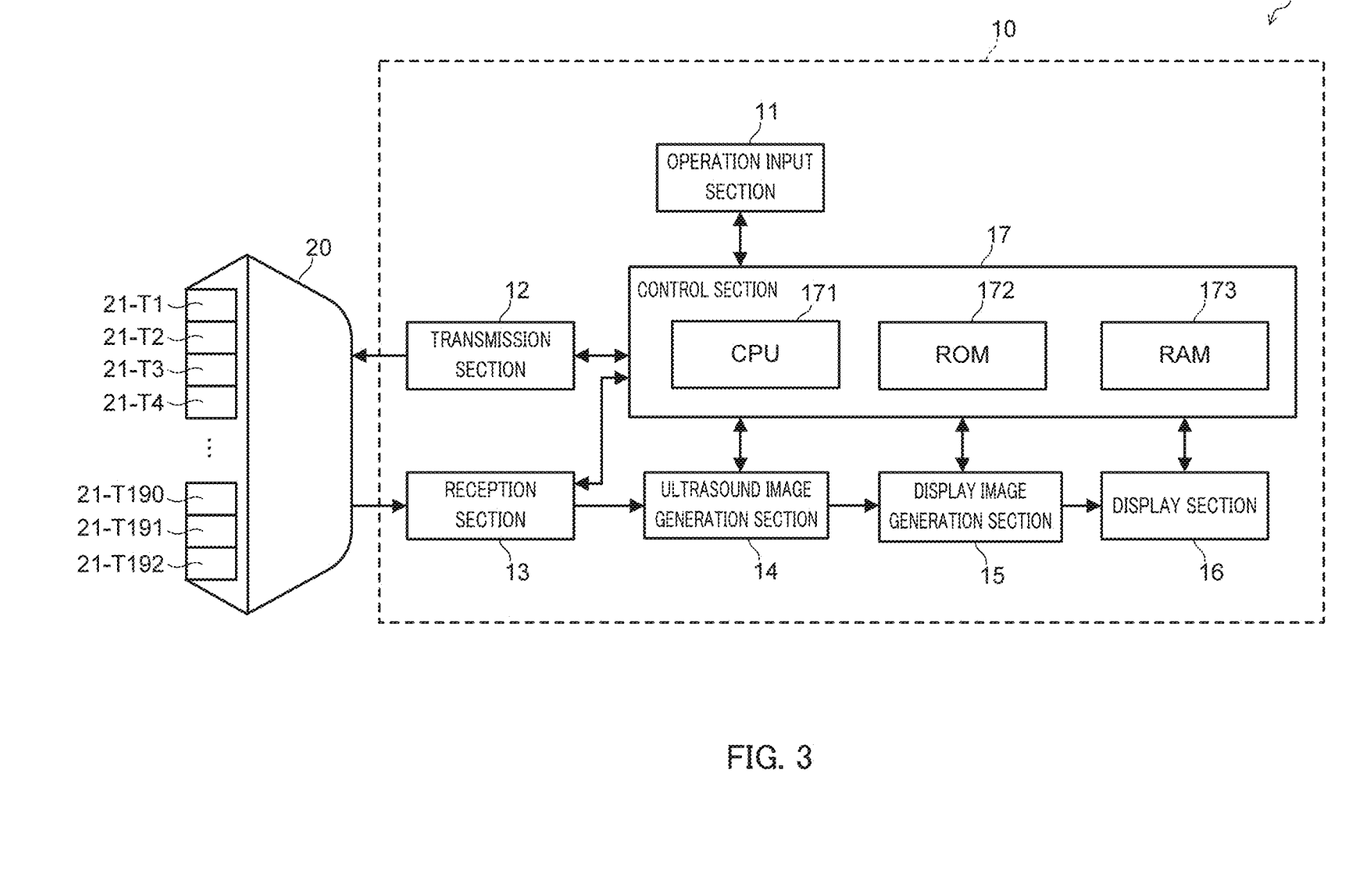
FIG. 3 is a block diagram illustrating a configuration example of main part of a control system of the ultrasound diagnostic apparatus according to the embodiment of the present invention.

FIG. 2 illustrates an exemplary external view of ultrasound diagnostic apparatus 1. FIG. 3 is a block diagram illustrating a configuration example of main part of a control system of ultrasound diagnostic apparatus 1.

Ultrasound diagnostic apparatus 1 is an apparatus that visualizes the shape, conditions or behavior of an inside of a subject as an ultrasound image. As illustrated in FIG. 2, ultrasound diagnostic apparatus 1 includes ultrasound diagnostic apparatus main body 10 and ultrasound probe 20, and ultrasound diagnostic apparatus main body 10 and ultrasound probe 20 are connected to each other via cable 30.

Ultrasound probe 20 functions as an acoustic sensor that transmits an ultrasound beam (here, approximately 1 to 30 MHz) into a subject (for example, a human body), receives an ultrasound echo resulting from part of the transmitted ultrasound beam reflected in the subject, and converts the ultrasound echo into an electric signal.

As ultrasound probe 20, any probe such as a convex probe, a linear probe, a sector probe, or a three-dimensional (3D) probe is applicable. Note that, in FIGS. 2 and 3, for convenience of description, only one ultrasound probe 20 is illustrated, but ultrasound diagnostic apparatus 1 typically includes plural types of ultrasound probes 20.

Ultrasound probe 20 is configured to include a plurality of piezoelectric elements 21-T1 to 21-T192 (here, 192 piezoelectric elements) for interconversion of the ultrasound and electric signals, and a channel switching section (e.g., multiplexer) (not illustrated) for switching control to turn on and off a driving state of each of the plurality of piezoelectric elements 21-T1 to 21-T192. In the following, piezoelectric elements 21-T1 to 21-T192 are referred to as "piezoelectric element 21" when they are not distinguished from each other.

Each piezoelectric element 21 of ultrasound probe 20 converts a voltage pulse generated by ultrasound diagnostic apparatus main body 10 (transmission section 12) into an ultrasound beam, transmits the ultrasound beam into a subject, receives a reflected-wave beam generated by reflection of the ultrasound beam in the subject, converts the reflected-wave beam into an electric signal (hereinafter referred to as "reception signal"), and outputs the reception signal to ultrasound diagnostic apparatus main body 10 (reception section 13).

The plurality of piezoelectric elements 21-T1 to 21-T192 are arranged in an array along a scanning direction, for example. Incidentally, the on and off of the driving state of each of the plurality of piezoelectric elements 21-T1 to 21-T192 is switched and controlled successively along the scanning direction individually or in units of blocks by control section 17. Thus, in ultrasound probe 20, the ultrasound is transmitted and received so as to scan in the subject.

Ultrasound diagnostic apparatus main body 10 includes operation input section 11, transmission section 12, reception section 13, ultrasound image generation section 14, display image generation section 15, display section 16, and control section 17.

Transmission section 12, reception section 13, ultrasound image generation section 14, and display image generation section 15 are configured of dedicated or general-purpose hardware (electronic circuitry) such as a Digital Signal Processor (DSP), an Application Specific Integrated Circuit (ASIC), a Programmable Logic Device (PLD) according to each processing, and realize each functions in cooperation with control section 17.

Operation input section 11 accepts, for example, a command instructing a start of a diagnosis or the like or an input of information related to the subject. Operation input section 11 includes, for example, an operation panel with a plurality of input switches, a keyboard, and a mouse. Incidentally, operation input section 11 may be formed by a touchscreen provided integrally with display section 16.

Transmission section 12 is a transmitter that sends out a voltage pulse that is a driving signal to ultrasound probe 20 in accordance with an instruction of control section 17. Transmission section 12 is configured to include, for example, a high-frequency pulse oscillator and a pulse setting section. Transmission section 12 adjusts a voltage pulse generated by the high-frequency pulse oscillator to a voltage amplitude, a pulse width, and a sending-out timing set by the pulse setting section, and sends out the voltage pulse for each channel of ultrasound probe 20.

Transmission section 12 includes the pulse setting section for each of a plurality of channels of ultrasound probe 20 and is configured such that the voltage amplitude, the pulse width, and the sending-out timing of the voltage pulse can be set for each of the plurality of channels. For example, transmission section 12 sets appropriate delay times for the plurality of channels to change a target depth or generate different pulse waveforms.

Reception section 13 is a receiver that performs a reception process on a reception signal related to an ultrasound echo generated by ultrasound probe 20 in accordance with an instruction of control section 17. Reception section 13 is configured to include a preamplifier, an AD conversion section, a reception beamformer, and the like.

The preamplifier of reception section 13 amplifies a reception signal related to a weak ultrasound echo for each channel, and the AD conversion section of reception section 13 converts the reception signal into a digital signal. In addition, the reception beamformer of reception section 13 unifies reception signals of the plurality of channels by phasing addition of reception signals of the respective channels, to thereby generate acoustic line data.

Ultrasound image generation section 14 acquires a reception signal (acoustic line data) from reception section 13 and generates an ultrasound image (i.e., tomographic image) of the inside of the subject.

For example, ultrasound image generation section 14 temporally continuously accumulates, in a line memory, a signal intensity of an ultrasound echo detected after ultrasound probe 20 transmits a pulsed ultrasound beam in a depth direction. In addition, along with scanning of the inside of the subject by using the ultrasound beam from ultrasound probe 20, ultrasound image generation section 14 successively accumulates the signal intensities of the ultrasound echoes at scanning positions in the line memory, to thereby generate two-dimensional data used as a frame unit. Further, ultrasound image generation section 14 generates an ultrasound image indicating a two-dimensional structure in a cross section that includes a transmission direction and the scanning direction of the ultrasound by converting the signal intensity of the two-dimensional data into a luminance value.

In addition, ultrasound image generation section 14 performs a correction process on the reception signal acquired from reception section 13 and thus may include, for example, an envelope detection circuit for envelope detection on the reception signal to be acquired from reception section 13, a logarithmic compression circuit for logarithmic compression on the signal intensity of the reception signal detected by the envelope detection circuit, and a dynamic filter that is a band-pass filter having a frequency characteristic is changed according to the depth and for removing a noise component included in the reception signal.

Display image generation section 15 acquires data of the ultrasound image from ultrasound image generation section 14 and generates a display image including a display area of the ultrasound image. Display image generation section 15 then sends out data of the generated display image to display section 16. Display image generation section 15 successively updates a display image at every acquisition of a new ultrasound image from ultrasound image generation section 14, and displays the display image on display section 16 in a moving image format.

Further, when a probe element check of ultrasound probe 20 is executed, display image generation section 15 generates a display image indicating a check result of the probe element check in accordance with an instruction of control section 17 (described later with reference to FIGS. 8, 9, and 10).

Display section 16 is configured of, for example, a liquid crystal display, an organic EL display, or an HMI device such as a CRT display. Display section 16 acquires the data of the display image from display image generation section 15 and displays the display image in accordance with an instruction of control section 17.

Control section 17 controls operation input section 11, transmission section 12, reception section 13, ultrasound image generation section 14, display image generation section 15, and display section 16 according to the respective functions, and thereby performs the total control of ultrasound diagnostic apparatus 1.

Control section 17 includes, for example, CPU (Central Processing Unit) 171 as an arithmetic/control device, ROM (Read Only Memory) 172 and RAM (Random Access Memory) 173 as main storage devices. ROM 172 stores therein a basic program and basic setting data. CPU 171 reads out a program corresponding to a processing content from ROM 172, loads the program into RAM 173, and executes the loaded program to centrally control the operation of each of the function blocks (operation input section 11, transmission section 12, reception section 13, ultrasound image generation section 14, display image generation section 15, and display section 16) of ultrasound diagnostic apparatus main body 10.

[Detailed Configuration of Control Section 17]

Next, with reference to FIGS. 4 to 10, a detailed configuration of control section 17 will be described. Here, a description will be given of only the configuration of control section 17 that functions at the time of probe element check.

Figure 4:
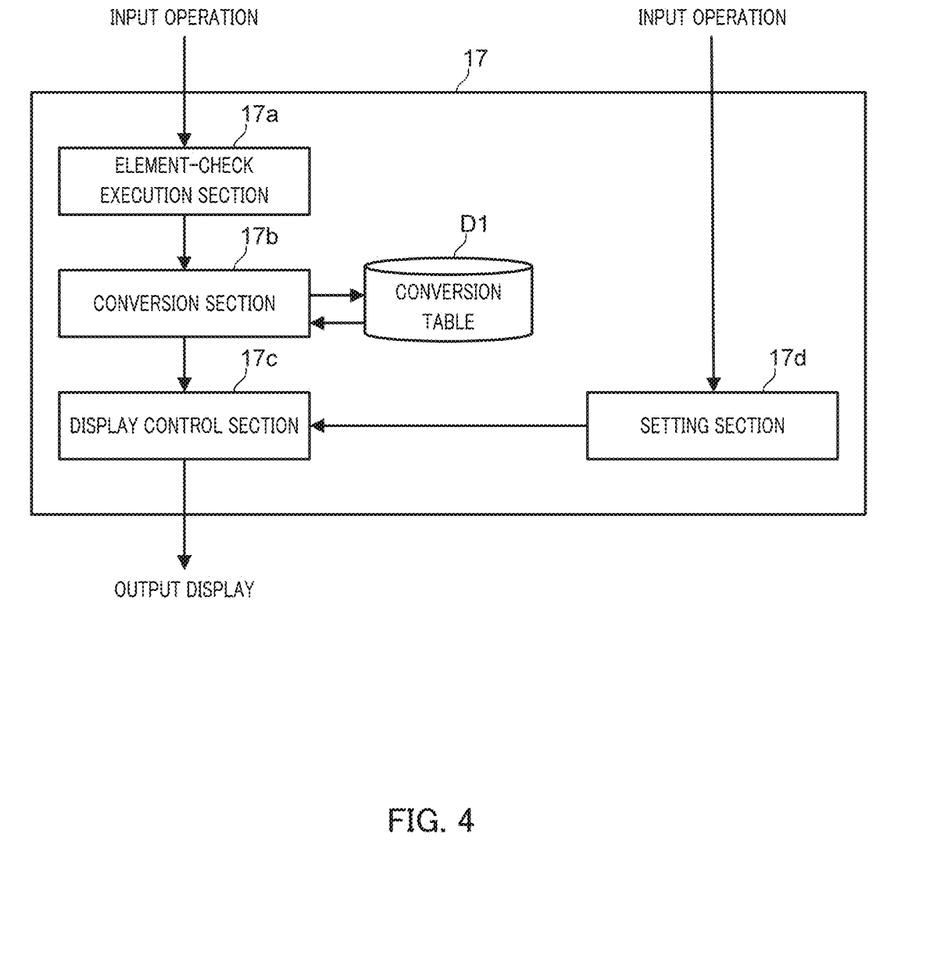
FIG. 4 illustrates a detailed configuration example of a control section according to the embodiment of the present invention.
Figure 5:
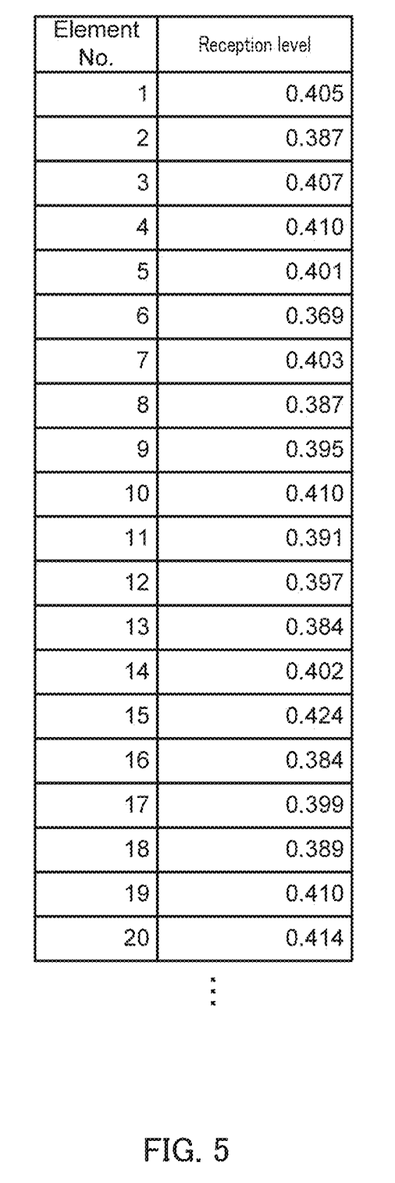
FIG. 5 illustrates a signal feature (reception level) of a reception signal obtained by a probe element check in the ultrasound diagnostic apparatus according to the embodiment of the present invention.
Figure 6:
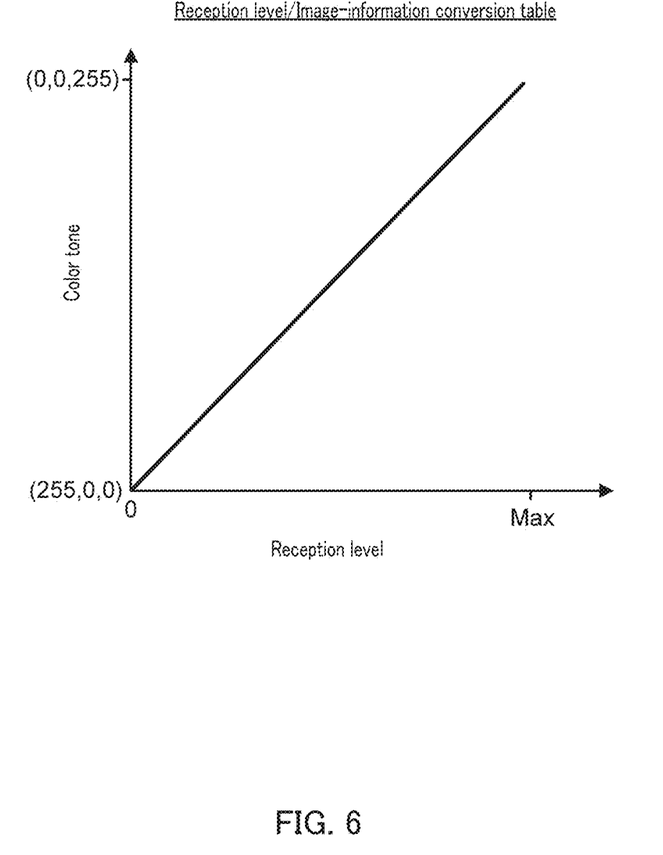
FIG. 6 illustrates a configuration example of a reception level/image-information conversion table according to the embodiment of the present invention.

FIG. 4 illustrates a detailed configuration example of control section 17. FIG. 5 illustrates a signal feature (here, reception level [dB]) of a reception signal obtained by the probe element check. FIG. 6 illustrates a configuration example of reception level/image-information conversion table D1 referred to by conversion section 17*b*.

Figure 7:
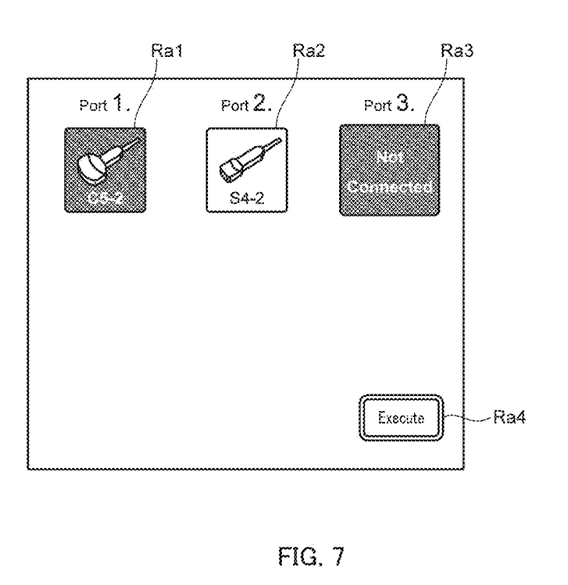
FIG. 7 illustrates an exemplary display screen that receives a type of an ultrasound probe subject to the probe element check in the ultrasound diagnostic apparatus according to the embodiment of the present invention.

FIG. 7 illustrates an exemplary display screen that receives a type of ultrasound probe 20 subject to the probe element check. FIG. 8 illustrates an exemplary display screen related to a check result of the probe element check. FIG. 9 illustrates an exemplary display screen related to a detailed check result of the probe element check. FIG. 10 illustrates an exemplary screen transition of a display screen when executing the probe element check. The display screens of FIGS. 7 to 9 are images for displaying generated by display image generation section 15 in accordance with an instruction of control section 17 (display control section 17*c*).

Control section 17 includes element-check execution section 17*a*, conversion section 17*b*, display control section 17*c*, and setting section 17*d*. Further, a storage section (e.g., ROM 172) of control section 17 includes reception level/image-information conversion table D1 to be referred to when conversion section 17*b* is operated.

<Element-Check Execution Section 17*a*>

Element-check execution section 17*a* causes transmission and reception of the ultrasound for the probe element check with respect to each of piezoelectric elements 21-T1 to 21-T192 included in ultrasound probe 20.

For example, after receiving from a user, selection of a type of ultrasound probe 20 subject to the probe element check (e.g., convex probe, linear probe, sector probe, or 3D probe) and/or a port number of ultrasound diagnostic apparatus main body 10 to which ultrasound probe 20 subject to the probe element check is connected, element-check execution section 17*a* executes the probe element check upon input of an execution command of the probe element check from the user.

In the display screen illustrated in FIG. 7, for example, element-check execution section 17*a* receives, from the user, the port number of ultrasound diagnostic apparatus main body 10 to which ultrasound probe 20 subject to the probe element check is connected.

Incidentally, in the display screen illustrated in FIG. 7, Ra1, Ra2, and Ra3, respectively represent icons for receiving, from the user, the port number of ultrasound diagnostic apparatus main body 10 subject to the probe element check. Further, Ra4 represents an icon for accepting, from the user, input of the execution command of the probe element check. Meanwhile, the display screen illustrated in FIG. 7 is displayed when, for example, an item of the probe element check is selected in a maintenance-top screen of FIG. 10.

Element-check execution section 17*a* controls, for example, the channel switching section (not illustrated) of ultrasound probe 20 to switch piezoelectric element 21 subject to the check among piezoelectric elements 21-T1 to 21-T192 successively along the scanning direction individually or in units of blocks (i.e., units of channels). Element-check execution section 17*a* then controls transmission section 12 and reception section 13, respectively, to cause them to transmit and receive the ultrasound with respect to piezoelectric element 21 subject to the check. Thus, the probe element check is executed on all of piezoelectric elements 21-T1 to 21-T192 included in ultrasound probe 20.

A method of the probe element check may be any publicly known aspect. In ultrasound diagnostic apparatus 1 according to the present embodiment, the probe element check of ultrasound probe 20 is executed by airborne radiation. In this method, the transmission and reception of the ultrasound is performed with respect to piezoelectric element 21 while an ultrasound transmission and reception surface of ultrasound probe 20 is exposed to the air, and a deterioration degree of piezoelectric element 21 is determined based on a signal intensity of an ultrasound echo (hereinafter may be referred to as a "reception level") reflected from an acoustic lens of ultrasound probe 20. That is, in this method, piezoelectric element 21 which is considerably deteriorated is detected as a piezoelectric element with a small reception level.

Generally, it is possible to determine the deterioration degree of piezoelectric element 21 based on whether ultrasound with an appropriate sound pressure intensity can be sent out when a driving signal is supplied from transmission section 12 to piezoelectric element 21, and whether piezoelectric element 21 can generate a reception signal with an appropriate signal intensity when an ultrasound echo from the inside of the subject is reached with respect to piezoelectric element 21, and thus, a reception level obtained by the probe element check with the airborne radiation is a total value thereof.

For example, element-check execution section 17*a* outputs a reception level obtained, by the airborne radiation, in each of piezoelectric elements 21-T1 to 21-T192 included in ultrasound probe 20 as a check result (see FIG. 5).

Meanwhile, in the probe element check, in addition to the reception level, signal features such as frequency characteristics (e.g., center frequency and frequency band) of the reception signals of respective piezoelectric elements 21-T1 to 21-T192, a variation in the signal intensities of the reception signals among piezoelectric elements 21-T1 to 21-T192, and a variation in frequency characteristics of the reception signals among piezoelectric elements 21-T1 to 21-T192 may also be a check target.

<Conversion Section 17*b*>

At the time of probe element check, conversion section 17*b* converts the signal feature (in the present embodiment, reception level) of the reception signal obtained in each of piezoelectric elements 21-T1 to 21-T192 included in ultrasound probe 20 into image information indicating a deterioration degree of piezoelectric element 21 separately.

Here, the "image information indicating a deterioration degree of piezoelectric element 21" is, for example, information for defining an image color corresponding to the deterioration degree of piezoelectric element 21. "The image information indicating a deterioration degree of piezoelectric element 21" specifies the image color of each piezoelectric element 21 to be mapped in probe-condition mapping image Rb1 of FIG. 8.

Conversion section 17*b* according to the present embodiment, determines the image information indicating the deterioration degree of each piezoelectric element 21 from the reception level of each piezoelectric element 21 obtained by the element check (see FIG. 5), by using reception level/ image-information conversion table D1 (see FIG. 6).

In reception level/image-information conversion table D1 of FIG. 6, reception levels obtained by the element check are classified with color information of 256 tones from blue to red, and a level of the deterioration degree is expressed by the tone of the image color. That is, the larger the reception level obtained by the element check (i.e., no deterioration proceeds), the larger the blue density is expressed, whereas as the reception level obtained by the element check becomes smaller (i.e., as deterioration proceeds), the smaller the blue density is expressed so as to approach the red density. This allows providing the user with probe-condition mapping image Rb1 in which the details of the deterioration degree of piezoelectric element 21 are intuitively understandable from the image color.

A correspondence relation between the reception level stored in reception level/image-information conversion table D1 and the image color is preferably set in advance based on a correspondence relation between a reception level specified by experimentation or simulation and a deterioration degree of piezoelectric element 21. Thus, the image color of piezoelectric element 21 converted by reception level/image-information conversion table D1 can be an objective indicator of the deterioration degree of piezoelectric element 21.

Alternatively, conversion section 17b may express the deterioration degree of piezoelectric element 21 by a pattern or the like of the image, instead of the image color. In addition, when converting the deterioration degree of piezoelectric element 21 into the image information, conversion section 17b may use, instead of using low data of the reception level obtained by the element check, normalized data obtained by a normalization process on the low data. Further, in a case where, in addition to the reception level, the signal features such as the frequency characteristics are also evaluated in the element check, conversion section 17b may determine the image information indicating the deterioration degree of piezoelectric element 21 from the total evaluation result thereof.

Besides, conversion section 17b preferably has a function of generating warning information (e.g., warning information display image Rb3 of FIG. 8) related to the need for repair of ultrasound probe 20, in addition to the function of generating the image information for probe-condition mapping image Rb1. This allows providing the user with the total determination result related to the need for the repair of ultrasound probe 20.

Such functions can be realized, as well as the function of generating the image information for probe-condition mapping image Rb1, by using information on reception levels of piezoelectric elements 21-T1 to 21-T192 included in ultrasound probe 20, the reception levels being obtained at the time of probe element check. Specifically, conversion section 17b may be configured to generate such warning information on the basis of, for example, the number of piezoelectric elements 21 whose deterioration degrees are determined as proceeding to be equal to or greater than a threshold value among piezoelectric elements 21-T1 to 21-T192, a mean value of the deterioration degrees of piezoelectric elements 21-T1 to 21-T192, and/or the like.

<Display Control Section 17c>

Figure 8:
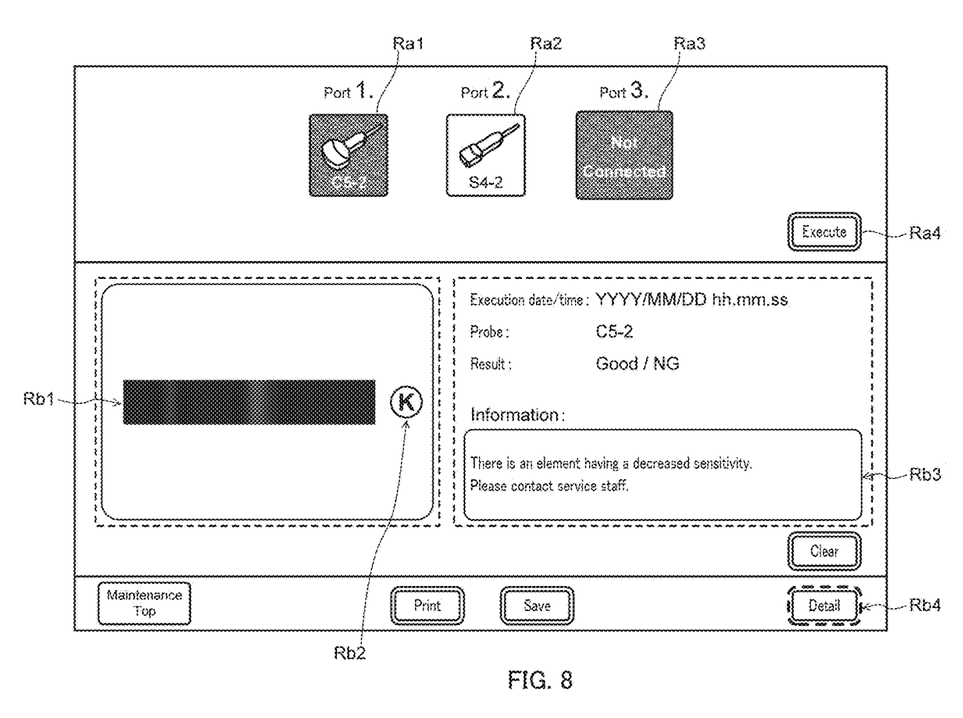
FIG. 8 illustrates an exemplary display screen related to a check result of the probe element check in the ultrasound diagnostic apparatus according to the embodiment of the present invention.
Figure 9:
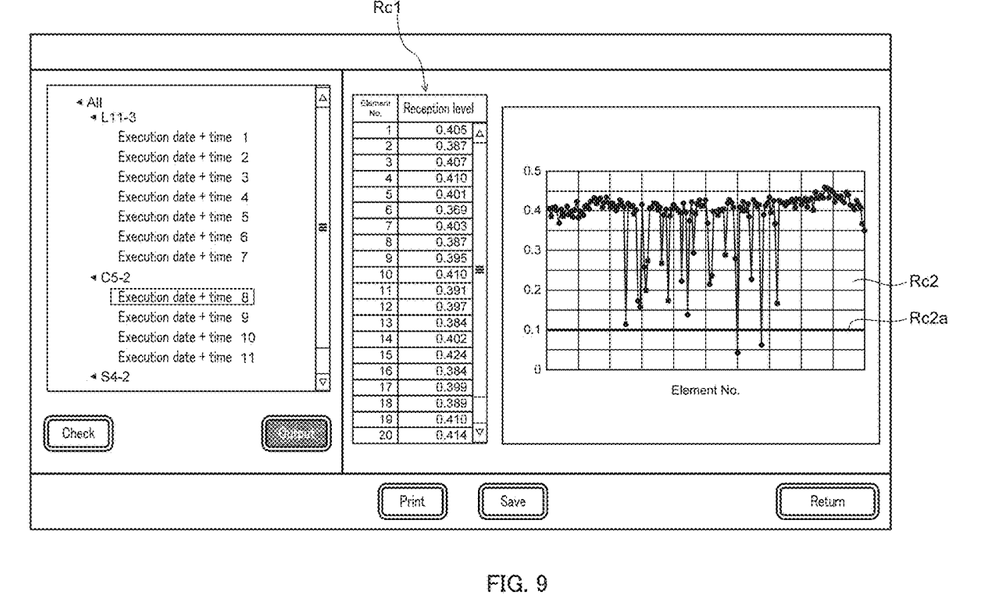
FIG. 9 illustrates an exemplary display screen related to a detailed check result of the probe element check in the ultrasound diagnostic apparatus according to the embodiment of the present invention.
Figure 10:
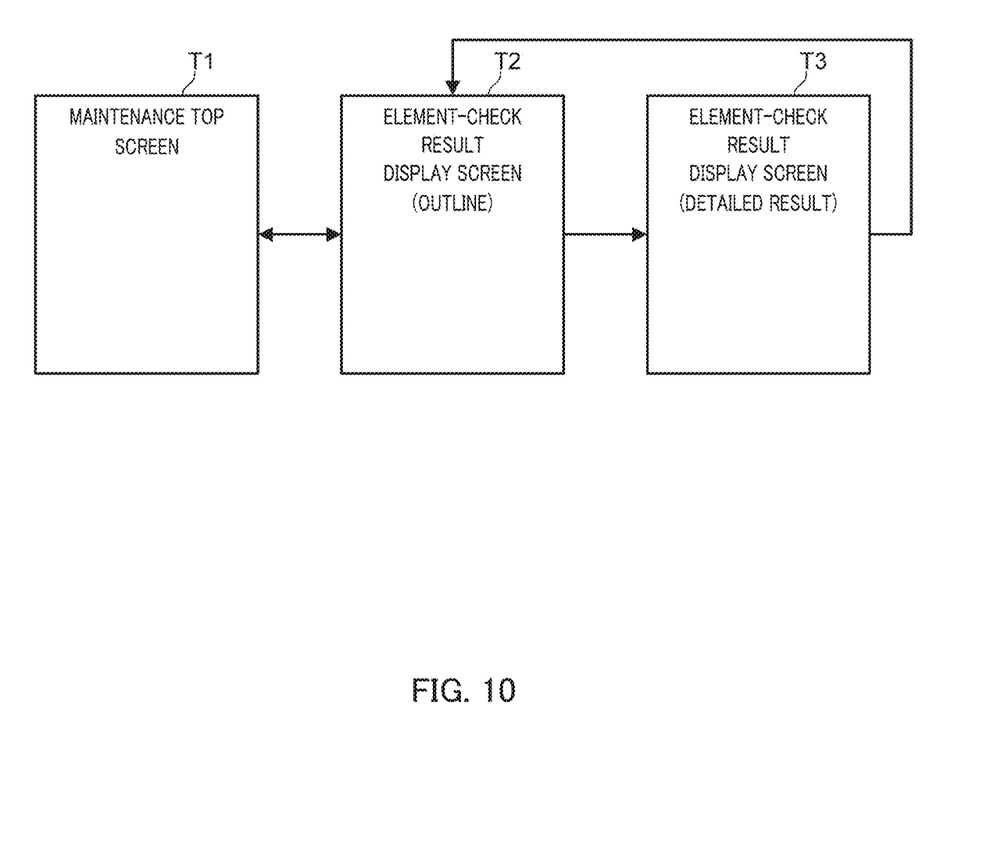
FIG. 10 illustrates an exemplary screen transition of a display screen when executing the probe element check in the ultrasound diagnostic apparatus according to the embodiment of the present invention.

When the probe element check is executed in element-check execution section 17a, display control section 17c controls display image generation section 15 to display a display image related to a check result (see FIGS. 8 and 9).

In order to provide a display screen by which common users can more intuitively understand the check result of the probe element check, display control section 17c according to the present embodiment is configured to firstly display a display screen related to an outline result illustrated in FIG. 8 when the probe element check is executed in element-check execution section 17a. In addition, display control section 17c displays a display screen related to the detailed result illustrated in FIG. 9 when a detailed content browsing operation is made by the user on the display screen related to the outline result.

Display control section 17c displays, on the display screen related to the outline result (see FIG. 8), for example, probe-condition mapping image Rb1 indicating the outline result of the element check, guide image Rb2 related to probe-condition mapping image Rb1, warning information display image Rb3, detailed result browsing icon Rb4, and the like.

Here, probe-condition mapping image Rb1 is an image generated using a result of the conversion in conversion section 17b (i.e., image information, which is generated by conversion section 17b, indicating the deterioration degree of each piezoelectric element 21) and is an image expressed in a bar form by mapping images indicating the deterioration degrees of respective piezoelectric elements 21-T1 to 21-T192 included in ultrasound probe 20 in a row according to an arrangement of piezoelectric elements 21-T1 to 21-T192 in ultrasound probe 20.

In probe-condition mapping image Rb1, an image indicating a deterioration degree of one piezoelectric element 21 is expressed, for example, as a single linear image extending longitudinally of the image color determined by conversion section 17b. Additionally, images indicating deterioration degrees of 192 pieces of piezoelectric elements 21-T1 to 21-T192 are arranged laterally in the display screen to constitute probe-condition mapping image Rb1. In probe-condition mapping image Rb1 of FIG. 8, piezoelectric elements 21 without deterioration among piezoelectric elements 21-T1 to 21-T192 are expressed by blue images, and piezoelectric elements 21 that are considerably deteriorated are expressed so as to approach a red image from the blue image according to deterioration degrees thereof. Further, in probe-condition mapping image Rb1 of FIG. 8, a right end side corresponds to piezoelectric element 21-T1 on the channel-1 side of ultrasound probe 20, whereas a left end side corresponds to piezoelectric element 21-T192 on the channel-192 side of ultrasound probe 20.

That is, display control section 17c makes it possible for the user, by using probe-condition mapping image Rb1, to intuitively understand to what extent and which position of piezoelectric element 21 is deteriorated in a case where piezoelectric element 21 that is considerably deteriorated is present in piezoelectric elements 21-T1 to 21-T192 included in ultrasound probe 20. In addition, this also makes it possible to grasp collectively piezoelectric elements 21 that are considerably deteriorated among piezoelectric elements 21-T1 to 21-T192 included in ultrasound probe 20, such as deterioration degrees of neighboring piezoelectric elements 21.

Guide image Rb2 is an image displayed in the vicinity of probe-condition mapping image Rb1 and indicating a correspondence relation between an arrangement direction of piezoelectric elements 21-T1 to 21-T192 in probe-condition mapping image Rb1 and an actual arrangement direction of piezoelectric elements 21-T1 to 21-T192 in ultrasound probe 20. FIG. 8 illustrates, as an example of guide image Rb2, a mark of "K" displayed at a position adjacent to a right side of probe-condition mapping image Rb1, and the mark of "K" indicates an actual side of piezoelectric element 21-T1 of ultrasound probe 20. Generally, a scanning direction (right to left or left to right) when an ultrasound image is generated can be changed by the user setting, and, along this direction, the arrangement direction of piezoelectric elements 21-T1 to 21-T192 in probe-condition mapping image Rb1 is reversed. From the viewpoint of suppressing misunderstanding relating to the position of piezoelectric element 21 caused by such a reverse, display control section 17c according to the present embodiment displays guide image Rb2, referring to the setting content related to the scanning direction stored in RAM 172.

Warning information display image Rb3 is warning information on the need for repair of ultrasound probe 20. In FIG. 8, as an example of such warning information display image Rb3, an aspect is illustrated in which a content suggesting the need for the repair of ultrasound probe 20 is displayed when even one piezoelectric element 21 of piezoelectric elements 21-T1 to 21-T192 included in ultrasound probe 20 with the deterioration proceeding to a predetermined threshold value is present. Display control section 17c displays warning information display image Rb3 based on the warning information generated by conversion section 17b.

Detailed result browsing icon Rb4 is an icon for accepting a request to browse the detailed result of the probe element check from the user. For example, when an input operation is performed for detailed result browsing icon Rb4, display control section 17c transits a display from the display screen related to the outline result illustrated in FIG. 8 to the display screen related to the detailed result illustrated in FIG. 9.

Display control section 17c displays, on the display screen related to the detailed result (see FIG. 9), list image Rc1 individually displaying the reception level obtained by each of piezoelectric elements 21-T1 to 21-T192 and graph image Rc2 graphically indicating the reception level obtained by each of piezoelectric elements 21-T1 to 21-T192, for example. In FIG. 9, display control section 17c displays, on graph image Rc2, for example, as reference information regarding the need for repair, the threshold value of the reception level (i.e., reception level at which repair is strongly recommended) Rc2a.

In general, since it is difficult to display reception levels of all piezoelectric elements 21-T1 to 21-T192 included in ultrasound probe 20 in one screen as a list, control section 17c typically controls the display of list image Rc1 so that piezoelectric element 21 to be displayed can be switched through scrolling and/or selection operations of the user. In other words, list image Rc1 is an auxiliary image for when the user wishes to check individually a deterioration degree of any of piezoelectric elements 21-T1 to 21-T192.

<Setting Section 17d>

Setting section 17d receives an input operation of the user and allows a display mode of the display screen for displaying the result of the probe element check to be customized according to preference of the user. Setting section 17d notifies display control section 17c of the display mode of the display image that has been changed in setting by the input operation of the user, and then display control section 17c controls display image generation section 15 so that the content in setting is reflected.

An example of a target for which setting section 17d sets it to be changeable includes, for example, the image color (i.e., RGB value) for expressing a deterioration degree of piezoelectric element 21 used in probe-condition mapping image Rb1. For example, setting section 17d may set the image color to be changeable into a mode in which a deterioration degree of piezoelectric element 21 is expressed in gray scale so as to be displayed in white when piezoelectric element 21 is not deteriorated and to be displayed in a color approaching black as the deterioration of piezoelectric element 21 proceeds.

Another example of the target for which setting section 17d sets it to be changeable includes, for example, an image pattern of guide image Rb2 indicating the arrangement direction of piezoelectric elements 21-T1 to 21-T192 in probe-condition mapping image Rb1. In one example, setting section 17d may set the image pattern of guide image Rb2 to be changeable from the K-mark image, into an image indicating a channel number for visually recognizing which position of probe-condition mapping image Rb1 corresponds to which channel, or an image of an arrow by which whether the channel-1 side is the left or right in probe-condition mapping image Rb1 can be recognized.

Setting section 17d may also set a display position of guide image Rb2 to be changeable. For example, setting section 17d may set the display position of guide image Rb2 to be changeable, from an adjacent position on the right side of probe-condition mapping image Rb1 into an adjacent position on the left side of probe-condition mapping image Rb1, an adjacent position on a lower side of probe-condition mapping image Rb1, or the like.

[Effect]

As described above, ultrasound diagnostic apparatus 1 according to the present embodiment includes, element-check execution section 17a that causes each of a plurality of piezoelectric elements 21-T1 to 21-T192 included in ultrasound probe 20 to execute transmission and reception of an ultrasound for a probe element check;

conversion section 17b that converts signal features of reception signals obtained respectively in the plurality of piezoelectric elements 21-T1 to 21-T192 at the time of the probe element check into information about images indicating deterioration degrees of the plurality of piezoelectric elements 21, separately; and display control section 17c that displays, based on a result of the conversion in conversion section 17b, a probe-condition mapping image expressed in a bar form by mapping the images indicating the deterioration degrees of the plurality of piezoelectric elements 21-T1 to 21-T192 in a row according to an arrangement of the plurality of piezoelectric elements 21-T1 to 21-T192 in ultrasound probe 20.

Thus, according to ultrasound diagnostic apparatus 1 of the present embodiment, the user can grasp the deterioration states of the entirety of piezoelectric elements 21-T1 to 21-T192 included in ultrasound probe 20, in a detailed and intuitive manner, to what extent and which position of piezoelectric element 21 is deteriorated.

Although embodiments of the present invention have been described and illustrated in detail, the disclosed embodiments are made for purpose of illustration and example only and not limitation. The scope of the present invention should be interpreted by terms of the appended claims.

INDUSTRIAL APPLICABILITY

According to the ultrasound diagnostic apparatus according to the present disclosure, it is possible to provide a user with information related to a check result of a probe element check in a more intuitively understandable manner.

What is claimed is:

1. An ultrasound diagnostic apparatus for obtaining a tomographic image of a subject by transmitting and receiving an ultrasound with an ultrasound probe, the ultrasound diagnostic apparatus comprising:

a hardware processor that:

causes each of a plurality of piezoelectric elements included in the ultrasound probe to execute transmission and reception of an ultrasound for a probe element check;

converts signal features of reception signals obtained respectively in the plurality of piezoelectric elements at the time of the probe element check into information about images indicating deterioration degrees of the plurality of piezoelectric elements, separately; and displays, based on a result of the conversion, a probe-condition mapping image expressed in a bar form by mapping the images indicating the deterioration degrees of the plurality of piezoelectric elements in a row according to an arrangement of the plurality of piezoelectric elements in the ultrasound probe, wherein the hardware processor displays a guide image in the vicinity of the probe-condition mapping image, the guide image indicating a correspondence relation between an arrangement direction of the plurality of piezoelectric elements in the probe-condition mapping image and an arrangement direction of the plurality of piezoelectric elements in the ultrasound probe, and wherein the hardware processor sets a display position of the guide image relative to a display position of the probe-condition mapping image to be changeable by an input operation of a user.

2. The ultrasound diagnostic apparatus according to claim 1, wherein the hardware processor expresses each of the images indicating the deterioration degrees by an image color according to the deterioration degree.

3. The ultrasound diagnostic apparatus according to claim 2, wherein the hardware processor classifies the deterioration degrees into at least three levels and expresses a level of each of the deterioration degrees by a tone of the image color.

4. The ultrasound diagnostic apparatus according to claim 2, wherein the hardware processor sets the image color according to the deterioration degree to be changeable by a second input operation of the user.

5. The ultrasound diagnostic apparatus according to claim 1, wherein the hardware processor sets an image pattern of the guide image to be changeable by a second input operation of the user.

6. The ultrasound diagnostic apparatus according to claim 5, wherein the hardware processor sets the image pattern of the guide image to be changeable by the second input operation of the user between a plurality of different types of image patterns, each of which indicates in respective different manners the correspondence relation between the arrangement direction of the plurality of piezoelectric elements in the probe-condition mapping image and the arrangement direction of the plurality of piezoelectric elements in the ultrasound probe.

7. The ultrasound diagnostic apparatus according to claim 1, wherein the hardware processor displays a list image individually displaying the signal features of the reception signals obtained respectively in the plurality of piezoelectric elements, in a case where a detailed content browsing operation from the user is received in a screen displaying the probe-condition mapping image.

8. The ultrasound diagnostic apparatus according to claim 7, wherein each of the signal features of the reception signals includes information on a signal intensity of the reception signal.

9. The ultrasound diagnostic apparatus according to claim 1, wherein the hardware processor generates warning information on a need for repair of the ultrasound probe based on the signal features of the received signals obtained respectively in the plurality of piezoelectric elements, and displays the generated warning information.

10. The ultrasound diagnostic apparatus according to claim 1, wherein the hardware processor executes the probe element check upon input of an execution command of the probe element check from the user.

11. A method of controlling an ultrasound diagnostic apparatus for obtaining a tomographic image of a subject by transmitting and receiving an ultrasound with an ultrasound probe, the method comprising:

causing each of a plurality of piezoelectric elements included in the ultrasound probe to execute transmission and reception of an ultrasound for a probe element check;

converting signal features of reception signals obtained respectively in the plurality of piezoelectric elements at the time of the probe element check into information about images indicating deterioration degrees of the plurality of piezoelectric elements, separately;

displaying, based on a result of the conversion, a probe-condition mapping image expressed in a bar form by mapping the images indicating the deterioration degrees of the plurality of piezoelectric elements in a row according to an arrangement of the plurality of piezoelectric elements in the ultrasound probe;

displaying a guide image in the vicinity of the probe-condition mapping image, the guide image indicating a correspondence relation between an arrangement direction of the plurality of piezoelectric elements in the probe-condition mapping image and an arrangement direction of the plurality of piezoelectric elements in the ultrasound probe, and setting a display position of the guide image relative to a display position of the probe-condition mapping image to be changeable by an input operation of a user.

12. A non-transitory computer-readable recording medium storing therein a computer readable program for controlling an ultrasound diagnostic apparatus for obtaining a tomographic image of a subject by transmitting and receiving an ultrasound with an ultrasound probe, the program causing a computer to perform processing comprising:

causing each of a plurality of piezoelectric elements included in the ultrasound probe to execute transmission and reception of an ultrasound for a probe element check;

converting signal features of reception signals obtained respectively in the plurality of piezoelectric elements at the time of the probe element check into information about images indicating deterioration degrees of the plurality of piezoelectric elements, separately;

displaying, based on a result of the conversion, a probe-condition mapping image expressed in a bar form by mapping the images indicating the deterioration degrees of the plurality of piezoelectric elements in a row according to an arrangement of the plurality of piezoelectric elements in the ultrasound probe;

displaying a guide image in the vicinity of the probe-condition mapping image, the guide image indicating a correspondence relation between an arrangement direction of the plurality of piezoelectric elements in the probe-condition mapping image and an arrangement direction of the plurality of piezoelectric elements in the ultrasound probe, and setting a display position of the guide image relative to a display position of the probe-condition mapping image to be changeable by an input operation of a user.

\* \* \* \* \*